United States Patent [19]

Nau et al.

[11] Patent Number: 5,029,065
[45] Date of Patent: Jul. 2, 1991

[54] CONTROL SYSTEM FOR A SAMPLE PREPARATION SYSTEM

[75] Inventors: Vance J. Nau, Cupertino; Keith H. Grant, Newark, both of Calif.

[73] Assignee: Ciba-Geigy Corporation, Ardsley, N.Y.

[21] Appl. No.: 341,301

[22] Filed: Apr. 20, 1989

Related U.S. Application Data

[63] Continuation of Ser. No. 942,196, Dec. 16, 1986, abandoned.

[51] Int. Cl.$^5$ .............................................. G05B 19/00
[52] U.S. Cl. ..................................... 364/146; 364/192
[58] Field of Search .............................. 364/140–147, 364/191–193, 469–473, 476, 477, 474.01, 167.01

[56] References Cited

U.S. PATENT DOCUMENTS

| | | | |
|---|---|---|---|
| 4,281,379 | 7/1981 | Austin | 364/171 |
| 4,328,550 | 5/1982 | Weber | 364/171 |
| 4,484,286 | 11/1984 | Nagamine et al. | 364/474 |
| 4,490,781 | 12/1984 | Kishi et al. | 364/191 |
| 4,519,026 | 5/1985 | Nozawa et al. | 364/171 |
| 4,521,860 | 6/1985 | Kanematsu | 364/171 |
| 4,547,854 | 10/1985 | Hashimoto et al. | 364/171 |
| 4,603,285 | 7/1986 | Matsuura et al. | 364/474 |

Primary Examiner—Allen MacDonald
Attorney, Agent, or Firm—Ronald C. Fish

[57] ABSTRACT

A system for controlling an electromechanical system comprised of a number of electromechanical devices such as solenoid operated valves, motor, relays and other devices. The control system is comprised of a central processing unit and control software plus suitable interface circuitry to convert the digital data from the central processing unit into suitable control signals to operate the electromechanical devices. The control software is characterized by the ability to allow users to either select preprogrammed sequences of commands to be executed by the computer or to program unique sequence at either of two levels of complexity. User access privileges may defined by the system manager such that certain users may not be allowed to program their own sequences, while other users may be allowed to program their own sequences only on the first level of complexity but not the second, while a third group of users may be allowed to program on either of the programming levels or to run the preprogrammed sequence as defined by the system manager. The two levels of programming complexity are a high level and an expert level where the command set on the high level consists of a plurality of commands each of which represents a macro.

5 Claims, 6 Drawing Sheets

CONTROL SYSTEM FOR A SAMPLE PREPARATION SYSTEM

This application is a continuation of application Ser. No. 942,196, filed Dec. 16, 1986, abandoned.

BACKGROUND OF THE INVENTION

The invention pertains to the field of sample preparation systems, and more particularly, to the field of control systems for automated sample preparation systems.

In many industrial production facilities and laboratories, there is a need to assay sample chemicals being prepared, analyzed or otherwise processed. Such samples can come in many different forms. For example, they may be solid, liquid, two phase liquid or liquid-solid, and may or may not be highly viscous. Many types of assay systems require liquid samples of known viscosity and concentration. An example would be a liquid chromatography system.

Obviously, there is a need for systems which can prepare many different types of samples for assay by such machines. Preferably such systems are automatic in the sense that after the user defines the type of sample preparation needed, the system automatically carries out this processing on samples until told to stop or until the sample preparation runs out of samples.

Because of the many different types of sample formats and because of the many different types of sample preparation processes which exist for various types of assays, there is a need for flexibility and programmability in a control system for an automated sample preparation system. The user must be provided the facility with which the particular types of samples he or she intends to process may be prepared in a process for which the steps and sequences of steps are defined by the user. In this way the user can tailor the automatic sample preparation system for use in the environment peculiar to that particular user.

Prior art automatic sample preparation systems exist in the form of robots. One particular type of robot of which the applicants are aware is a robot manufactured by Zymark. These robots may be programmed to emulate all the movements a human being would make in doing a sample preparation process manually. Unfortunately, such systems are complicated and expensive and difficult to use because of the complexity of the mechanical machinery and control computers and software needed. Thus, a need has arisen for a control system for a sample preparation system which is flexible, programmable, easy to use, and relatively inexpensive to manufacture.

SUMMARY OF THE INVENTION

In accordance with the teachings of the invention, there is provided a control system for a sample preparation system to fully automate the system and allow users to program their own sample preparation procedures or to use preprogrammed procedures. Further, the control system allows a user acting as a system manager to define the necessary sample preparation procedures for various types of samples likely to be encountered. Then the system manager may lock out users without system manager privileges to prevent them from altering the procedures while allowing such users to use the procedures programmed for them by the system manager.

The control system of the invention allows user interaction with the system at three levels. At the first level, users may only give the sample identification (in embodiments with no bar code reader), the lot number to run, and the method of sample preparation will have been programmed into nonvolatile memory before the control system is obtained by the user or will have been previously programmed in by the system manager.

The next level of user interaction is a high level language level. At this level, the user has various high level sample preparation system control commands at his disposal. Such commands include fill, mix, isolate, flush, dilute, inject, wash, etc. Each of these commands represents a predetermined sequence of events which will be caused by the control system to happen in the sample preparation system when the particular command is executed in the course of performing a sample preparation procedure. The user at this level may string a series of such high level commands together into a sample preparation procedure and give it a name. Upon selection of a high level command, the control system would prompt the programmer for any necessary variables or parameters, such as solvent selection, volumes, flow rates, mixing times, etc. Thereafter, by identifying the particular procedure the user wishes to run, the same sequences of events may be caused to occur in the sample preparation system of the invention. Some of the high level commands have parameters which are accessible to the user and may be set to accommodate the particular needs of the user. These parameters allow the user to control, for example, the amount of time a mixing step is carried out and the level of energy that is input to the mixer by the homogenizer.

The key to breaking up sample preparation procedures into a series of standard preparation steps, which can be chained or re-chained together in any sample preparation procedure, is to design the hardware and software control logic to allow each standard preparation step and each programmed series of standard preparation steps to be completely independent of the preceding or following step or series of steps. For example, upon completion of a dilution sequence or cup wash cycle, the diluent or wash solvent from a prior dilution or rinse should not be left in the instrument connecting tubings or modules. If there is such leftover solvent etc., it may inadvertently contaminate the next dilution or wash with the wrong or an undesired solvent. If this undesired solvent could not be removed from all tubings and connections prior to the next step or sequence of steps, the next step would be restricted to using a solvent deemed compatible with the undesired solvent and thereby place undesired restrictions on the next step.

At the most detailed level, the control system according to the invention provides the user access to and programmability for elemental operations of the type that are combined into the sequences which make up each high level command. Such elemental operations control individual events in the system such as the opening and closing of a particular valve, the turning on of the homogenizer, setting of the power level of the homogenizer, etc. The user may program the system at this level by stringing names. These sequences may be thought of as user definable high level commands, or "macros." The user may string any number of macros together to form a procedure which may then be labelled and executed by referring to it by its name.

DETAILED DESCRIPTION OF THE PREFERRED EMBODIMENT

Figure 1:
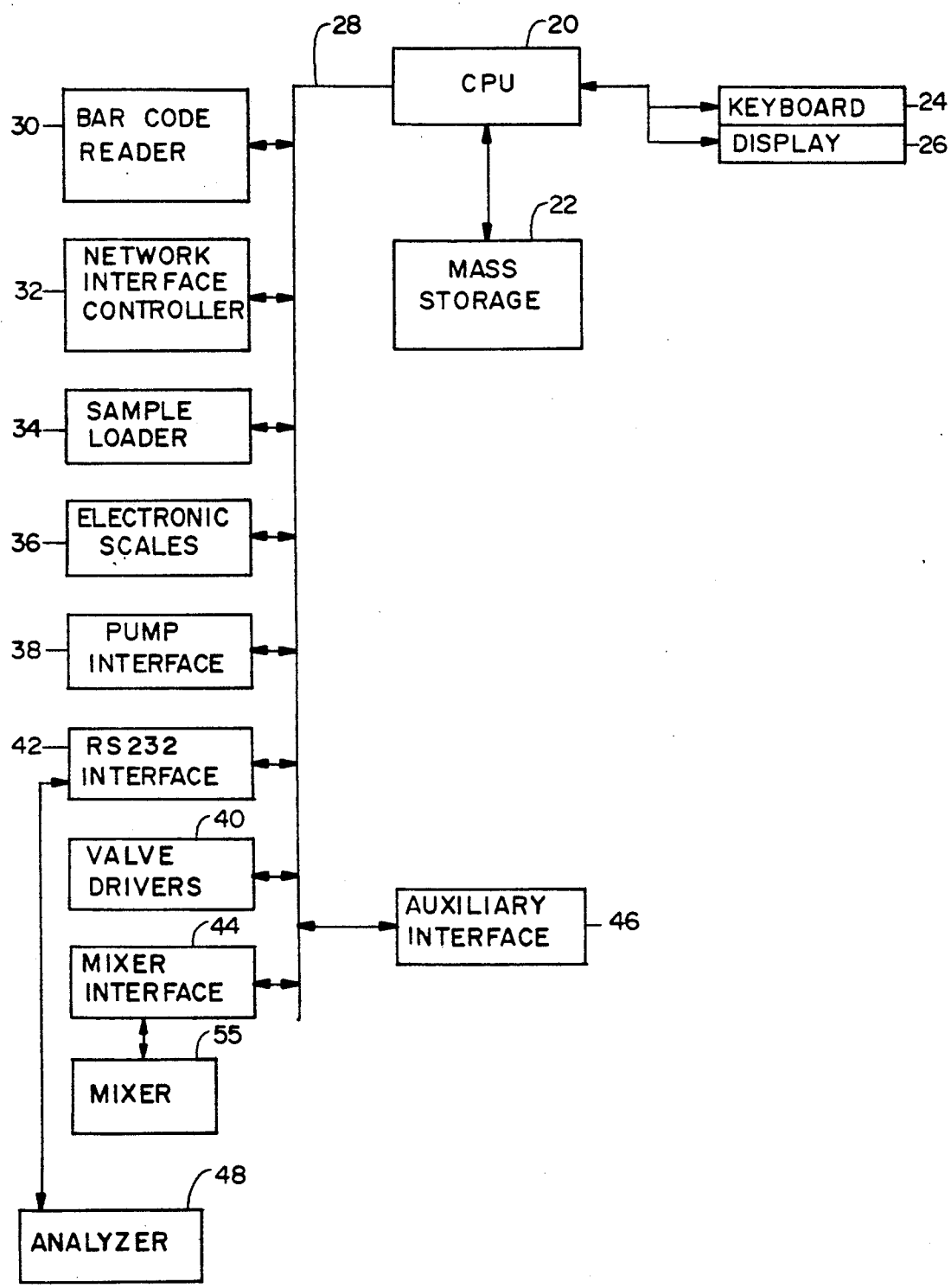
FIG. 1 is a block diagram of the hardware of the control system and the system electromechanical devices which are read and controlled by the control system.

FIG. 1 is a block diagram of the electronics of the control system in accordance with the teachings of the invention. The control system is centered around a CPU 20 which could be a microprocessor, personal computer, minicomputer, or mainframe. Included within the CPU block is RAM memory for storing programs and data while the computer is running. Mass storage of data, programs, and other information such as data bases, macros, user defined parameters, user defined sample processing routines, etc., is performed by mass storage unit 22. This unit could be a disk drive, tape transport, bubble memory, or any other bulk storage device with sufficient access speed and storage capacity for the particular application involved. The user controls the computer 20 through a terminal comprised of keyboard 24 and any type of display 26.

The computer 20 is coupled to the various operating units in the sample preparation system by bus 28. This bus 28 is actually comprised of the address, data, and control signal lines of the computer 20. The bus is coupled to the ports for addresses, data, and control signals such as read/write, interrupt, ready, etc. on the various drivers and interfaces to the various functional elements of the system. A more complete description of the sample preparation system for which the control system is intended to be used with is given in the following U.S. patent applications: "System for Preparation of Samples for Analysis" by Nau, Metzger, Grimm, Nohl, Ser. No. 942,197, filed Dec. 16, 1986, and "Sample Preparation Chamber with Mixer/Grinder and Sample Aliquot Isolation" by Nau, Metzger, Grimm, Andre, and Nohl, Ser. No. 942,198, filed Dec. 16, 1986, now U.S. Pat. No. 4,792,434, both of which are hereby incorporated by reference.

Because the sample preparation system is intended for use in applications where either the samples will be brought into the system in cups or other containers with bar codes thereon or pumped into the cup through 6-way valve, a bar code reader 30 is provided. This allows sample identification data such as lot number and batch number or other types of information pertaining to the incoming samples to be read from bar codes on the sample containers. This information may then be read by the computer 20 and stored in the mass storage unit 22 for later correlation with the test results for that group of samples. Bar code readers are known and systems for moving sample containers by bar code readers so that the bar codes may be read are also known.

In the preferred embodiment, a network interface controller 32 is provided to allow other computers and units on a network in the user facility such as terminals in the offices of scientists to offices, program the system or inquire as to the status of a particular sample preparation routine. Further, the users may have access to the data which resulted from a particular sample run. For the network interface, this user can have the sample data resulting from the assay of a particular lot of sample communicated directly into the data based in the other computer.

A sample loader 34 functions to mechanically load samples arriving in containers. The particular design of the sample loader is not critical to the invention. It may load sample from one or more containers brought in by the user such as a tray of test tubes into the sample preparation chamber. In such a system, the sample from each test tube would be loaded into the sample preparation chamber, homogenized, diluted, and pumped through the assay system. At some point in the process, the sample would be identified either by the user keying in the identification data or by the bar code reader 30 reading the bar code on the test tube. The analysis data from the assay would then be stored in the mass storage unit 22 along with the corresponding identification data. The sample loader would then load the sample from the next test tube into the sample preparation chamber, and the process would be completed for the sample from the next test tube. The design of such a sample loader is known and a commercially available unit which could be programmed to do the job would be the PRO/GROUP(tm) automatic assay machine available from Cetus Corporation in Emeryville, Calif. In alternative embodiments, the sample loader 34 could by any mechanical system which could take a cup like that used in the sample preparation chamber described in the patent applications incorporated by reference and attach it to the cap. Any mechanical arrangement that can load a copy from a tray, conveyor belt, or carousel of cups into mechanical, sealing engagement with the cap of the sample preparation chamber described in the patent applications incorporated by reference will suffice. In some embodiments, this unit may be omitted altogether where sample is pumped in from a process stream or injected from a 6-way valve coupled to a sample vat. The design of suitable sample loaders which will suffice to practice this aspect of the invention is known.

There is also provided electronic scales 36 in the preferred embodiment, these provide the facility for weighing of solid samples or samples which are too viscous to pump into the sample preparation chamber where such samples are placed manually in the sample preparation chamber. The purpose of weighing such samples is to provide the user with an indication of the amount of sample that has been placed in the sample preparation chamber. This is important because the samples will later be diluted with solvents or diluent to a user defined concentration. In order to do this property, the weight of sample in the sample preparation chamber prior to addition of the diluent must be known. The electronic scales also provide an RS232 or parallel interface to the computer 20 via the bus 28 so that the computer 20 may read the sample weight directly. The electronic scales may be eliminated in some embodiments. Without the electronic scales, if the user is dealing with a solid sample, the weight of sample placed in the sample preparation chamber must be keyed in by the user through the keyboard 24. A suitable electronic scale 36 would be the Mettler AE160 available from Mettler in Switzerland.

A pump interface 38 provides the facility for the computer 20 to control the reversible pump used in the sample preparation chamber. The pump motor may be a stepper motor or a D.C. servo motor with an optical or other type of encoder so that the pump interface circuit 38 can determine the position of the motor shaft at all times. Any type of motor with sufficient power and a system to positively control the pump shaft position or otherwise control the exact volume pumped will suffice. The pump interface obviously needs to be designed to interface between the particular type of pump motor and pump chosen and the particular type of computer 20 chosen.

Figure 2:
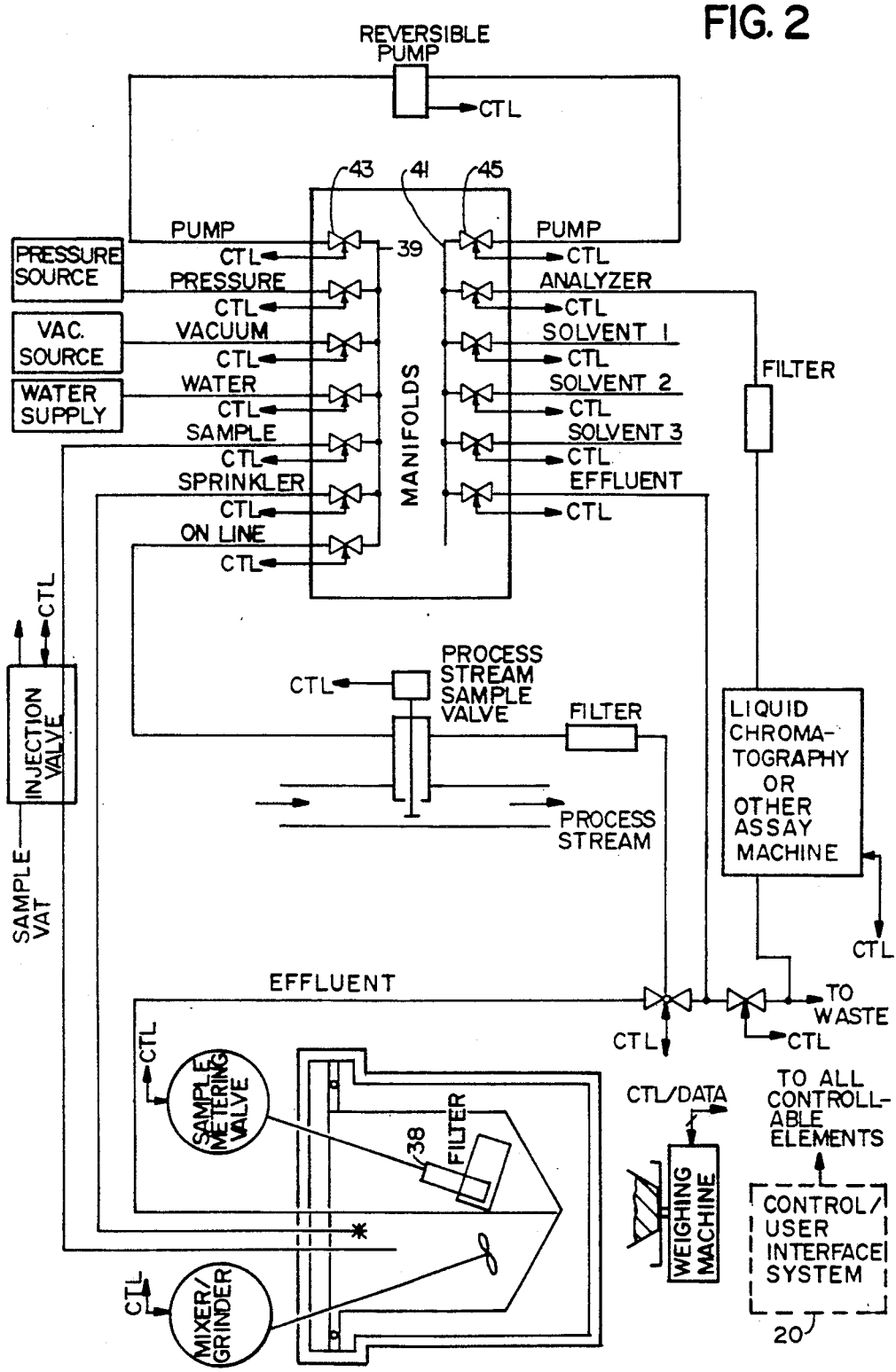
FIG. 2 is a schematic diagram of a typical sample preparation system which may be controlled by the control system of the invention.

FIG. 2 shows one embodiment of a sample preparation system with which the control system of the invention may be used. In this embodiment of the sample preparation system, the details of the structure and operation of which are as described in the patent applications incorporated herein by reference, two manifolds 39 and 41 are used as central terminals in what amounts to a fluid switching multiplexer. Each manifold is coupled to various sources of material or various destinations in the system by a plurality of remotely controllable valves of which valves 43 and 45 are typical. These valves are typically solenoid operated or pneumatically operated under the control of the computer 20. The purpose of the valve interface 40 in FIG. 1 is to electrically translate the address, data, and control signals on the bus 28 into the proper electrical or pneumatic control signals to cause the proper valve in the system to assume the proper state. Such interface circuits are well known for either solenoid operated valves or pneumatically operated valves. For example, in the case of solenoid operated valves, a motor controller chip can decode the address on the bus 28 and a data word indicating whether the valve is to be opened or closed along with an active write signal. All these signals define an action desired for a particular valve. The address specifies which valve is to be operated, and the active write signal indicates when the computer 20 is addressing a particular valve. The data word defines whether the valve is to be opened or closed or which of its multiple states to assume in the case of a multistate valve. The motor controller chip then activates a particular output signal line coupled to a solenoid driver such as a relay or a triac in such a manner as to cause the desired change in the state of the addressed valve.

In the case of pneumatic valves, the address, data and control signals are decoded, as above, but the activated output signal from the motor controller chip is used to control a pneumatic pressure source to either apply pneumatic pressure or remove it from the particular valve addressed.

Figure 3:
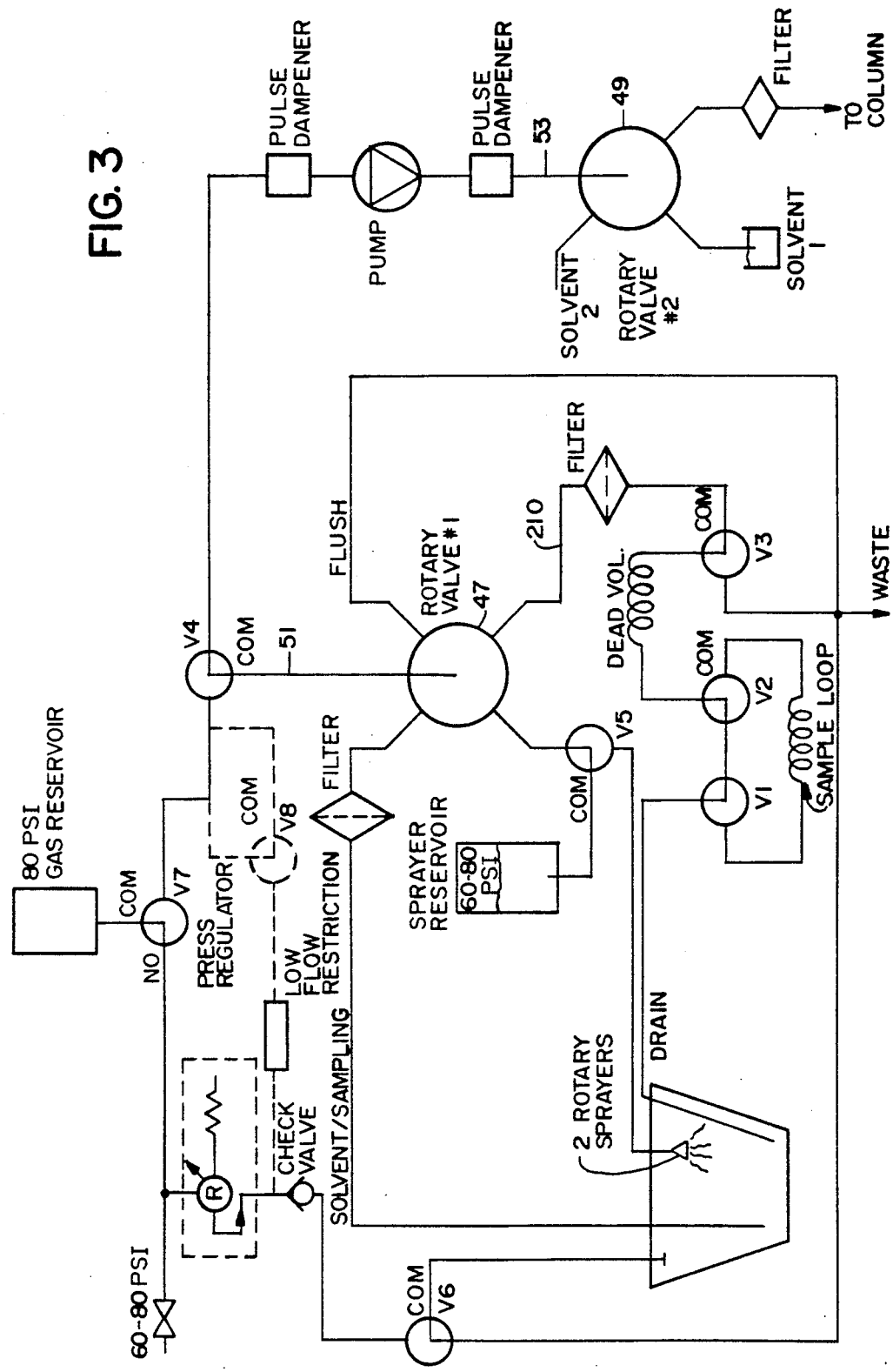
FIG. 3 is a schematic diagram of another embodiment of a sample preparation system which may be controlled using the control system of the invention.

FIG. 3 shows the preferred embodiment of the sample preparation system with which the control system in accordance with the teachings of the invention is used. The difference between this sample preparation system and the sample preparation system of FIG. 2 is that the manifolds 39 and 41 and the associated valves such as valves 43 and 45 are replaced with two rotary, multistate valves 47 and 49. All other details of the system structure and operation are as described in the patent applications incorporated by reference herein. Each of these valves has a central input pipe, pipes 51 and 53 respectively, which is connected to only one of a plurality of output ports coupled to various sources of material or destinations in the system. A stepper motor or D.C. servo motor with optical encoder is used to drive the valve to its various states. In such an embodiment, the valve drivers 40 are the interface circuits needed to control the stepper motors or D.C. servo motors. Integrated circuits for stepper motor control are commonly available. These circuits allow the computer 20 to send address and data words to the stepper motor controller after enabling the chip with a proper chip select signal. The address signals indicate which of the two rotary valves is being addressed, and the data words indicate the desired state in which the rotary valve is to be placed. Typically, these integrated stepper motor controllers have a command set. Typical commands include commands to start and stop the controlled motor, commands to control the acceleration and deceleration profiles to use, commands to control the step number to which the controlled motor's shaft is to be moved, and commands to read the particular step at which the controlled motor's shaft is currently resident. Such chips may be used to control the stepper motors used to drive the rotary valves 47 and 49. In the preferred embodiment of the sample preparation system, these rotary valves 47 and 49 are manufactured by Hamilton Company of Reno, Nev.

A typical D.C servo motor which could be used to drive the rotary valves 47 and 49 is manufactured by Galil Motion Control, Inc. of Mountain View, Calif. under the model delegation DMC 100. These servo motors have optical encoders which are used to provide feedback as to the shaft position to an interface board for the Galil motor plus motor controller chips for the other remotely controlled valves in the system.

The RS232 port interface 42 may be a simple commercially available UART. The analyzer 48 may be coupled to the computer 20 through the RS232 interface 42, or the network interface 32.

The mixer 55 in FIGS. 1 and 2 may be an ultrasonic mixer such as is made by Sonic and Materials of Danbury, Conn. under the trademark VIBRA CELL. In alternative embodiment, a high speed homogenizer could be used such as are made by Brinkman (shroud with a high speed rotating shaft therein rotating at 28,000 RPM, thereby creating a high shear in the liquid and disintegrating particles therein). These units come with their own interfaces which may be used for the mixer interface 44. The basic control functions needed to control the mixer are the time of mixing and the power level which controls the amount of turbulence generated in the liquid. The mixer interface will be necessary electronics to interface with the mixer control circuit for the selected mixer. The details of how to interface the computer 20 to the interface circuits that come with the mixers will be apparent to those skilled in the art. A good reference for interfacing computers such as the computer 20 to control external instrumentalities is Libes and Garetz, interfacing S-100/IEEE 696 Microcomputers, (Osborne/McGraw Hill 1981) which is hereby incorporated by reference. An auxiliary interface 46 is provided to allow the computer 20 to control external instrumentality such as valves, solenoids, etc. which are outside the sample preparation system. Typically, this interface will be digital, programmable ports such as are commonly available in integrated circuit form where the characteristics of the ports may be set by the user.

Figure 4:
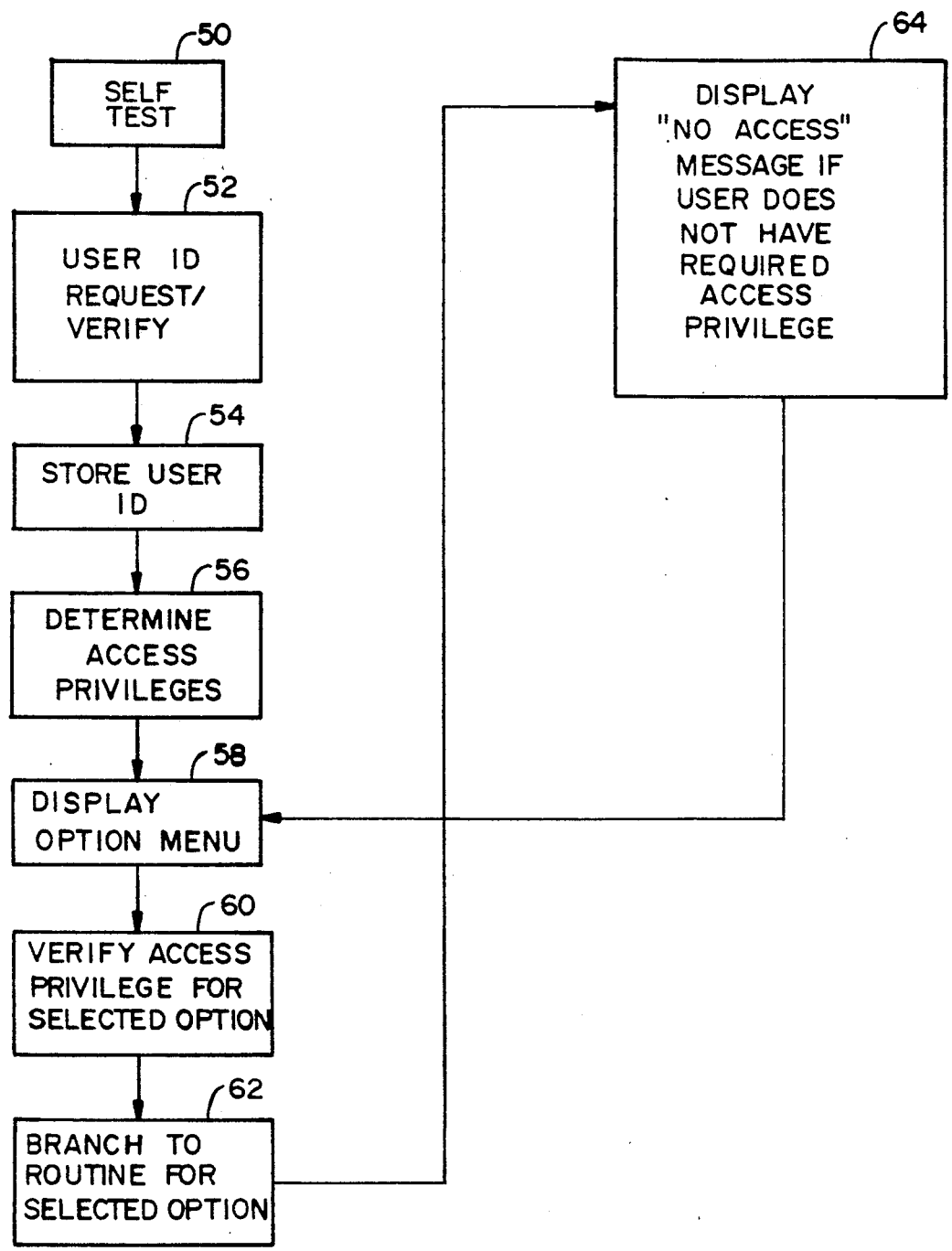
FIG. 4 is a flow diagram of the overall control flow of the control system software.

FIG. 4 is a high level functional diagram of the control program in the computer 20 which allows users to program and run their own sequences of events to be performed in the sample preparation system under control by the control system of the invention. The control program runs the user defined sequences by generating the proper control signals to cause the desired sequence of events to occur in said sample preparation system.

At power up in some embodiments, the system will perform a self test to verify the integrity of the system prior to performing any operations. This is symbolized by block 50. Next, the system displays a user identification request/sample identification request screen as symbolized by block 52 (hereafter references to blocks will be understood to mean reference to those source code computer instructions organized as routines and subroutines in the control program which perform the function indicated in the block referred to). The purpose of block 52 is to supply query fields on the terminal or display 26 for the user to respond to by filling in the requested data via the keyboard 24. The requested data is to identify the user, to give various data items regarding the sample, to give the data and the time and to identify the sequence the user desires to run. The data items regarding the sample to be filled in may include the sample ID, the sample weight, and the lot number from which the sample came. The user identification number is used by the control system to determine the access privileges which the user has.

The control system has three levels of access. At the simple level, the user may only run sequences that have been previously programmed by the system manager. At the high level, users having access privileges at this level may program their own sequences of events using commands from a high level language command set. These commands represent predetermined building block functions which are necessary to perform sample preparation. Such building block functions include: mix, isolate known sample volume, flush the remaining liquid out of the sample preparation chamber, release the isolated sample volume, dilute the sample volume with a user defined volume of a user identified solvent, pump the diluted sample to the analyzer, etc. At the expert level, users having access to this level may program their own "macros" using system commands at a more detailed level than the high level commands identified above. These more detailed commands allow the user to control the system at a finer level of resolution. For example, a typical command may be "open valve #1" or "rotate multiport value #2 to state #3." Each of the high level commands is comprised of a predetermined sequence of expert level commands.

The identification data entered by the user in block 52 via the keyboard 24 is stored on the mass storage device 22 in block 54. Next the system, in block 56, determines the access privileges of the user by comparing the user ID to the list of ID numbers supplied by the system manager for each level of access.

Block 58 represents the step of displaying an option menu by which the user, by selecting an option, may express a request regarding what the user wishes the system to do or what the user desires to do with the system. Typical menu options include: start, status, method, directory, report, load, print, system, control, defaults, functions, and options. The meaning of these options will be explained more below.

After the user has entered his or her request via the keyboard 24, the control system verifies that the user has the access privilege necessary to perform the function requested in block 60. If so, the control system branches to the routine which performs the desired function or provides the facility requested by the user in block 62. If the user does not have the required access privilege, a message to that effect is displayed in block 64, and processing proceeds to block 58.

Figure 5:
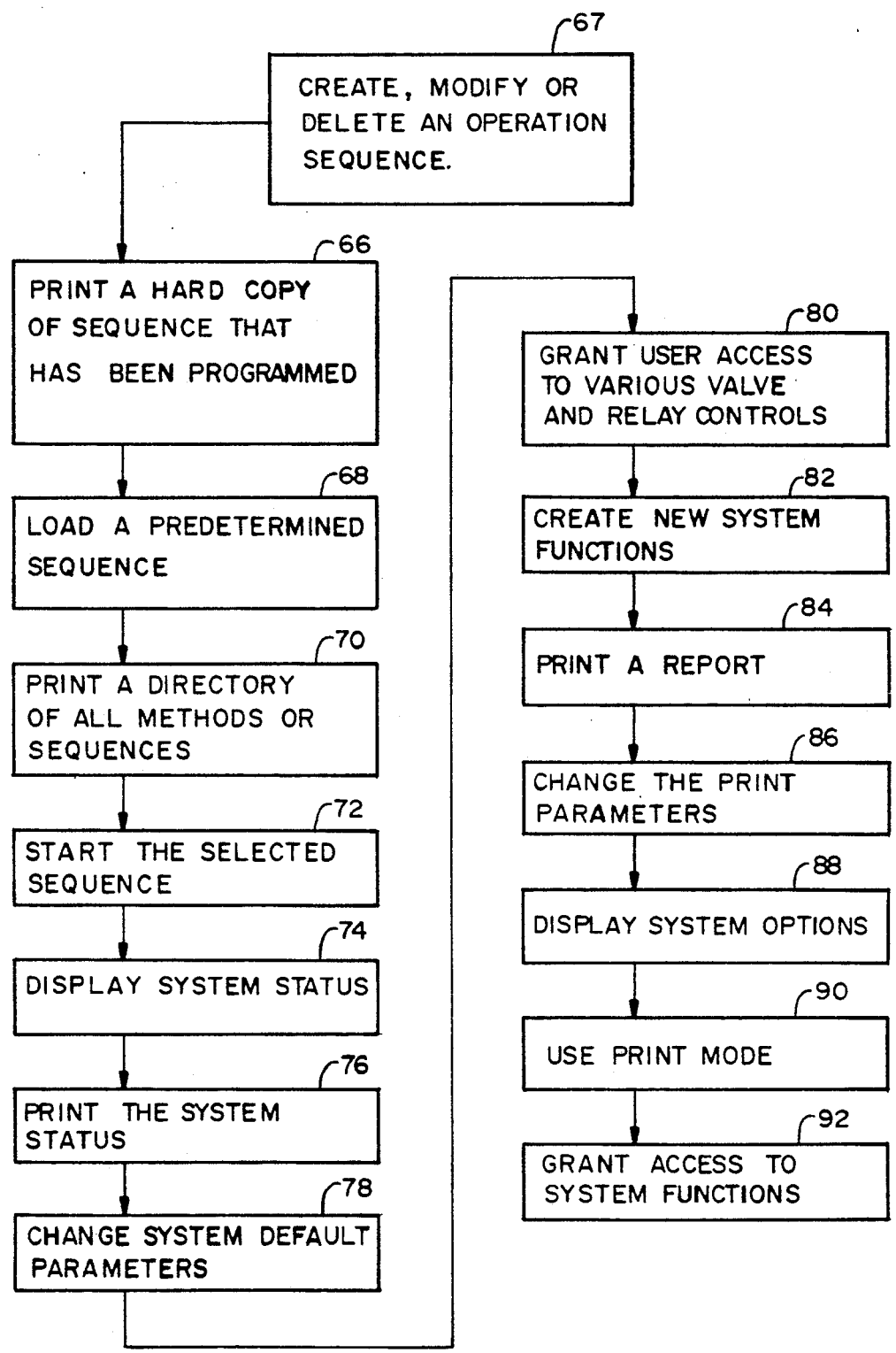
FIG. 5 is a flow diagram of the various routines of the control system of the invention.

Referring to FIG. 5 there shown a flow chart of the various routines which are available for selection by the user in Step 58 of FIG. 4. The first routine, symbolized by block 67, is routine which allows the user to create, modify, or delete an operation sequence. An operation sequence is a collection of commands which are executed by the central processing unit in order to generate control signals to control the electromechanical devices in the system. The control signals cause them to perform a physical sequence of events to process a sample where the sequence is defined by the particular sequence of commands in the program. The routine of block 67 allows the user to program his own sequences of commands at either of two levels of complexity. At a first level of complexity, the user may have access to a set of commands each of which represents a specified function that the system is capable of performing and each of which causes a predetermined sequence of events to occur in the proper order to cause the physical event symbolized by that command. The second level of complexity allows the user to have access to a set of commands which are very detailed. These commands each represent a single action or a very small group of actions that one or a very small group of electromechanical devices performs. Essentially, the commands at this second level are the component commands which are grouped together in a predetermined sequence to implement one of the commands on the first level. Essentially then, the commands on the first level are macros which are collections of commands on the second level but arranged in predetermined sequence for each particular command on the first level.

Block 66 is a routine which allows the user to print a hard copy of a sequence which has been programmed by the user.

Block 68 is a routine which allows the user to load a predetermined sequence, i.e., a method of sample preparation which has been preprogrammed by the system manager. The system manager is a user which has access to all functions of the system. That is, the system manager can define the access privileges of all the other users on the system, and he may program preprogrammed sequences which are available for certain users who are not allowed to program their own sequences. Block 68 is the routine which the user calls when one of these preprogrammed sequences is to be loaded.

Block 70 is a routine which allows the user to print a directory of all the methods or sequences which are stored in the system and available for execution. Block 72 represents a routine which allows the user to start the selected sample preparation routine and which causes the CPU to begin generating the control signals which cause the physical actions to occur.

Block 74 represents a routine which displays the system status. Block 76 is a routine which allows the user to print the system status which is displayed in the routine of Block 74.

Block 78 is a routine which allows the user to change the system default parameters. Typically, each command on either the first or second programming level will have parameters or arguments associated therewith. These arguments are variable values which define the specific manner in which the command is to be performed. For example, a mix command may have as an argument the power level at which the mix is to be performed, the time duration of the mix, and the rpm that the mixer is to use.

The routine represented by block 80 allows the user to have access to the various valve and relay controls such that the user may open certain valves or close certain relays manually by causing the CPU to generate the proper command to cause the proper operation of the valve, relay to other electromechanical device.

Block 82 represents a routine which allows the system manager to create new system functions.

Block 84 is a routine which allows the user to print a report. Such reports may consist of reports of user activity, the sequences which have been run, the volume of activity for a particular sequence, and so on. Block 86 is a routine which allows the user to change the print parameters. This routine allows the format of the report to be set such as margins, spacing, headers, and other types of formatting commands common to database report routines.

Block 88 is a routine which displays for the user the system operation which have been elected and which are operable.

Block 90 is a routine which allows the user to use the print mode of the system for various functions.

Block 92 is a routine which allows the system manager access to certain system functions.

Figure 6:
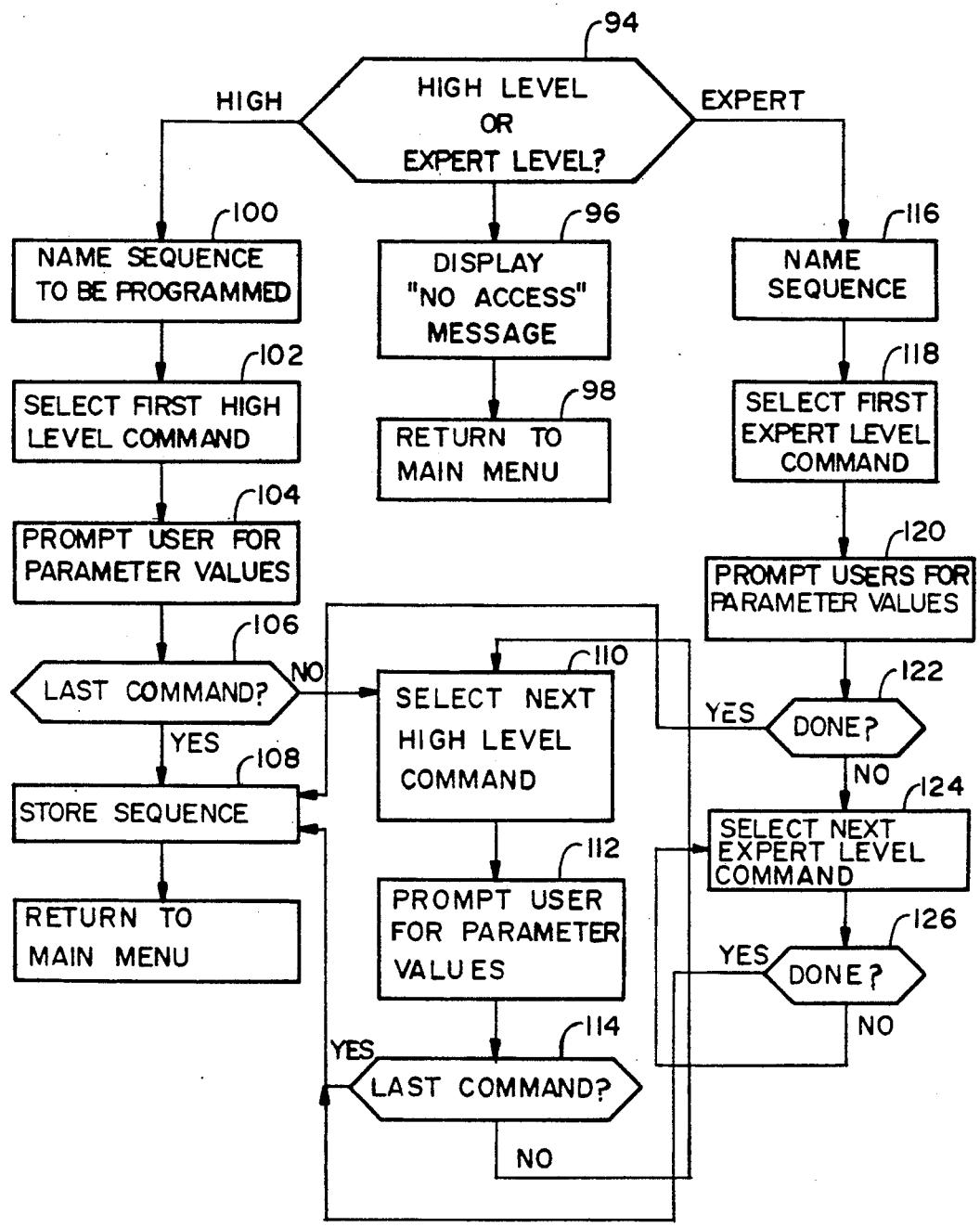
FIG. 6 is a flow diagram of the create, modify and delete routine of the control system of the invention that the allows a user to create new sequences of commands at either of two levels of detail and complexity.

Referring to FIG. 6 there is shown a more detailed flow diagram of the create, modify and delete routine of block 67 in FIG. 5. The first step when the user elects to program his own sequence is to inquire whether the user wishes to program on the first level or on the second level noted above. The first level will be called the high level for purposes here, and this level will provide the user access to the macro commands. The second level will be called the expert level and grants the user access to the detailed commands which essentially allow the user to define each valve opening and closing and each operation of each motor or other electromechanical device individually. The levels are named the high level and the expert level for purposes of indicating the relative amounts of skill needed to program on these levels. Programming at the high level is similar to calling subroutines or macros on any computer. Programming on the expert level is similar to programming in source code and requires a some programming skill and a great deal of knowledge regarding the hardware aspects of the system being programmed.

The process of determining which level the user wishes to have access to is symbolized by step 94. This step also determines the user's access privilege by checking the user's identification code and comparing it to a table or other such database defined by the system manager which indicates which users have access to the high level command set and which users have access to the expert level programming command set. If the user elects to program at the high level, the next step is symbolized by block 100. In this step, the user is prompted for a name for the sequence which he is about to program. After the sequence has been named, step 102 is performed wherein the user selects the first high level command which is to be executed in the sequence. In some embodiments, the list of high level commands from which the user may choose may be displayed and the user may simply choose a command by positioning the cursor on the proper command and pressing a select key. In other embodiments, the user may be required to know the high level commands and select the particular command desired by an acronym.

As noted above, most commands have certain parameters or arguments. Step 104 represents the process of prompting the user for parameter values for the command selected in step 102. Each command will have default parameters which are set by the user in step 78 of FIG. 5. If the user wishes to use the default parameters, he need do nothing in step 104. If however, the user wishes to define the specific manner in which the particular command is to be executed, when the parameters for that command may be adjusted in step 104.

After step 104 is performed, the control software causes the central processing unit to prompt the user to determine if the command just defined is the last command in the sequence. This step is symbolized by block 106 in FIG. 6. If the user is done picking commands, the processing proceeds to step 108 where the method is stored in permanent storage such as on a floppy disk or hard disk. Processing then returns to the main menu symbolized by block 58 in FIG. 4.

If the user is not finished programming, then processing proceeds form block 106 to block 110 where the user is prompted to select the next high level command in the sequence. Processing then proceeds to block 112 where the parameters for the command selected in block 110 are displayed and the user is prompted for new values for these parameters. If the user responds with new parameters, these are stored with the command as a permanent part of the sequence being programmed. After step 112 is performed, step 114 is performed to again to test for completion of programming. Step 114 represents the process of prompting the user to determine if the user is done programming. If he is, then processing continues at step 108 as described above to store the method. If the user is not done programming as determined in step 114, then processing returns to step 110 where the user is prompted to select the next command in the sequence.

Returning again for a moment to step 94 in FIG. 6, if the user is determined to have no access to either the high level or expert level programming command sets, then step 94 vectors processing to a step 96 wherein a "no access privilege for selected level" message is displayed on the terminal. Thereafter, in step 98, processing is returned to the main menu of step 58 in FIG. 4.

If the user selects the expert level for programming, a similar sequence of event occurs starting with step 116. There the user is prompted to name the sequence he is about to define. The next step, 118, prompts the user to select the first expert level command to be executed in the sequence. Then, in step 120, the user is prompted to select new parameters for the expert level command selected in step 118. Again, the expert level commands also have default values which may be altered by the user in step 120. Step 122 represents a test to determine if programming has been completed. If it has, then step 108 is performed as described above. If programming is not completed, processing proceeds to step 124. There the user is prompted to select the next expert level command and define the parameters for that command.

Step 126 represents a test to determine whether the user is done programming. If he is, then step 108 is performed and control is returned to the main menu. If the user is not done programming, then control returns to step 124 where the user is prompted to select the next expert level command.

Although the invention has been described in terms of the preferred and alternative embodiments detailed herein, those skilled in the art will appreciate that many modifications may be made. All such modifications are intended to be included within the scope of the claims appended hereto.

What is claimed is:

1. A control system including a computer for controlling under the direction of a user an apparatus having a plurality of interconnected electromechanical devices, chambers and fluid pathways comprising:

first means for running a plurality of preprogrammed sequences of commands to control a plurality of said electromechanical devices, said preprogrammed sequences of commands being nonalterable in the sense that said user cannot add, delete or change any command in the sequence, each said preprogrammed sequence of commands causing said plurality of electromechanic devices to cooperate to accomplish a particular overall function among a plurality of overall functions which said apparatus is capable of performing;

second means for receiving, storing, and running new sequences of commands selected by said user from a command set of a first complexity level hereafter called the "high" level, each said high level command for causing said control system to control one or more of said electromechanical devices to cause a high level event to occur, said high level event involving cooperation of several of said electromechanical devices to perform a "building block" function, where a building block function is defined as a function one or more of which are necessary to achieve one of the overall functions achieved by said apparatus when said control system performs any one of said preprogrammed sequences of commands run by said first means;

third means for receiving, storing and running new sequences of commands selected by said user from a command set of a second complexity level hereafter called the "expert" level, each said expert level command causing said control system to generate control signals to control an individual one of said electromechanical devices to do a single task, each said single task being one of a plurality of subtasks a collection of which comprises one of said building block functions carried out by one of said high level commands; and access control means for controlling whether said user is allowed to run only said preprogrammed sequences using said first means or is also allowed to define, store and run new sequences of commands using commands from said high level command set or said expert level command set or both using either said second means or said third means or both.

2. The apparatus of claim 1 wherein at least some of said commands at said high level and at said expert level have parameters and wherein said control system includes prompting means for prompting said user to supply any parameter values that pertain to a high level or expert level command selected by said user and for programming said command so selected with the user supplied parameter values.

3. The apparatus of claim 2 wherein said control system further comprises prompting means in each of said second and third means for prompting said user for entry of new commands at the appropriate complexity level and for storing commands so entered as a new sequence of commands wherein each said new sequence of commands is for causing a new predetermined sequence of events to be performed by said electromechanical devices.

4. The apparatus of claim 3 wherein said control system further comprises means for providing programmable access privileges for said user for determining whether said user is allowed to program with commands from either or both of said high level and expert level command sets and wherein said access control means further comprises prompting means for prompting said user for access privilege data in the form of a user identification code such that said access control means can determine from said user identification code the access privileges said user has to said high level and expert level command sets.

5. The apparatus of claim 4 wherein multiple users use said apparatus and wherein said access control means further comprises means for providing a first group of users the capability to run only said preprogrammed sequences of commands and for providing a second group of users the capability to program a new sequence of commands using commands from said high level command set and for providing the capability to a third group of users to program a new sequence of commands using commands from said expert command set.

* * * * *